(12) United States Patent
Furuki (10) Patent No.: US 8,080,408 B2
(45) Date of Patent: Dec. 20, 2011

(54) BIOASSAY SUBSTRATE AND BIOASSAY METHOD

(75) Inventor: Motohiro Furuki, Tokyo (JP)

(73) Assignee: Sony Corporation, Tokyo (JP)

( * ) Notice: Subject to any disclaimer, the term of this patent is extended or adjusted under 35 U.S.C. 154(b) by 331 days.

(21) Appl. No.: 11/778,474

(22) Filed: Jul. 16, 2007

(65) Prior Publication Data

US 2008/0014630 A1    Jan. 17, 2008

(30) Foreign Application Priority Data

Jul. 14, 2006   (JP) ................. P2006-194475

(51) Int. Cl.
*C12M 3/00*    (2006.01)
(52) U.S. Cl. ............ 435/287.2; 422/401; 422/407; 422/82.05; 422/82.11; 435/288.7; 436/809
(58) Field of Classification Search .............. None
See application file for complete search history.

(56) References Cited

U.S. PATENT DOCUMENTS

| | | | | |
|---|---|---|---|---|
| 5,738,825 | A | * | 4/1998 | Rudigier et al. ......... 422/82.11 |
| 6,083,763 | A | * | 7/2000 | Balch .................. 506/9 |
| 7,582,486 | B2 | * | 9/2009 | Gollier et al. ............. 436/164 |
| 7,799,885 | B2 | * | 9/2010 | Shustack et al. .......... 526/318.2 |
| 2003/0232384 | A1 | * | 12/2003 | Kocher et al. ............ 435/7.1 |
| 2004/0053337 | A1 | | 3/2004 | Yamazaki et al. |
| 2005/0025421 | A1 | * | 2/2005 | Caracci et al. ............ 385/37 |

FOREIGN PATENT DOCUMENTS

| | | |
|---|---|---|
| JP | 2002-253232 | 9/2002 |
| JP | 2003-035710 | 2/2003 |
| JP | 2003-107086 | 4/2003 |
| JP | 2003-156442 | 5/2003 |
| JP | 2003-262588 | 9/2003 |
| JP | 2005-249635 | 9/2005 |
| JP | 2005-345439 | 12/2005 |
| JP | 2005-538377 | 12/2005 |
| JP | 2006-017706 | 1/2006 |
| WO | 2005/010532 | 2/2005 |
| WO | 2005/114132 | 12/2005 |

OTHER PUBLICATIONS

Japanese Office Action issued on Sep. 2, 2008.

* cited by examiner

*Primary Examiner* — Chris L Chin
(74) *Attorney, Agent, or Firm* — K&L Gates LLP (57) ABSTRACT

A bioassay substrate and method thereof is provide. In the bioassay substrate, a sample solution is dripped onto a spot area to which a plurality of detection substances is fixed and an interaction between the detection substance and a target substance in the sample solution is detected by fluorescent intensity. The substrate includes: a predetermined number of the spot areas placed in a well arranged on the surface of the substrate; and a fine uneven structure continuously formed on a bottom surface configuring the spot areas.

3 Claims, 9 Drawing Sheets

BIOASSAY SUBSTRATE AND BIOASSAY METHOD

CROSS REFERENCES TO RELATED APPLICATIONS

The present application claims priority to Japanese Patent Application JP 2006-194475 filed in the Japanese Patent Office on Jul. 14, 2006, the entire contents of which being incorporated herein by reference.

BACKGROUND

The present application relates to a bioassay substrate for detecting interactions between substances. More specifically, the application relates to a bioassay substrate in which a sample solution is dripped onto a spot area to which a plurality of detection substances is fixed and interactions between the detection substance and a target substance in the sample solution is detected by fluorescent intensity, and a bioassay method using the substrate.

In recent years, in the fields of making drugs, clinical diagnosis, pharmacological genomics, forensic medicine, and so on, a bioassay substrate such as a DNA chip (or DNA microarray) and a protein chip is starting to be used for the analysis of gene variations, the analysis of SNPs (a single nucleotide polymorphism), the analysis of gene expression frequency, and the analysis of the interaction between substances.

Generally, on a bioassay substrate, a plurality of wells is provided in advance which is the site for interaction (such as hybridization), and a target detection substance (such as a probe nucleic acid) is fixed to every well. Then, a sample solution is dripped onto each of the wells, an interaction between the detection substance and a target substance contained in the sample is developed, and then the interaction is detected by fluorescent intensity, whereby exhaustive analysis is conducted.

In addition, as a preceding reference having the relevance to the application, for example, Patent Reference 1 (see JP-A-2003-107086) is exemplified. The Patent Reference 1 discloses a technique in which a frosted surface with nearly uniform micro portions is formed in an area for solidifying a nucleic acid probe to enhance detection accuracy.

In the case in which a detection substance is fixed to a substrate surface, it is necessary to fix it in a single layer. Thus, the amount of a detection substance fixable in a well is restricted. Therefore, the amount of interaction between the detection substance and the target substance is also restricted, which causes a problem that when a bioassay substrate is used to detect the interaction between the detection substance and the target substance, it is difficult to obtain a sufficient detected amount (such as fluorescent intensity).

In addition, when a related art bioassay substrate is used to detect the interaction between the detection substance and the target substance, the detection accuracy and the signal-to-noise ratio is not always enough.

SUMMARY

It is desirable to provide means for increasing the detected amount of interaction in the case in which a bioassay substrate is used to detect the interaction between a detection substance and a target substance, and to improve the detection accuracy and the signal-to-noise ratio thereof.

An embodiment provides a bioassay substrate in which a sample solution is dripped onto a spot area to which a plurality of detection substances is fixed and an interaction between the detection substance and a target substance in the sample solution is detected by fluorescent intensity, the substrate including: a predetermined number of the spot areas placed in a well arranged on the surface of the substrate; and a fine uneven structure continuously formed on a bottom surface configuring the spot areas.

For example, a micromachining technique such as lithography, etching, nanoimprint, and injection molding is used to continuously form the fine uneven structure in nano order in the spot area. Accordingly, since the surface area for fixing can be increased, the amount of fixing the detection substance in the spot area can be increased. Therefore, in the case in which a bioassay substrate is used to detect the interaction between the detection substance and the target substance, the detected amount of interaction (such as fluorescent intensity) can be increased, and the detection accuracy and the signal-to-noise ratio can be also improved.

At this time, it may be configured in which an equation expressed in Equation 1 is satisfied, where a track pitch length of the uneven structure is L, a wavelength of a fluorescent excitation ray emitted toward the bottom surface of the spot area is $\lambda(i)$, and a refractive index of the uneven structure is $n(i)$:

$$L < \lambda(i)/n(i). \qquad \text{Equation 1}$$

Generally, fluorescent excitation rays are emitted from a light source, they are focused by an iris lens disposed close to a substrate, and then they enter a spot area in a cone shape. On this account, some of excited rays enter the spot area at an angle. At this time, the fine uneven structure formed in the spot area functions as a diffraction grating, sometimes causing the diffracted light, or the reflected light affected by a reflective film formed right under the substrate surface. The caused diffracted light or the reflected light sometimes enters adjacent other spot areas.

In contrast to this, with the above configuration, the diffracted light or the reflected light can be prevented from entering from the other spot areas. Therefore, in the case in which a bioassay substrate is used to detect the interaction between the detection substance and the target substance, the detection accuracy and the signal-to-noise ratio can be improved.

Hereinafter, the technical terms according to an embodiment will be described.

The term "interaction" means that two substances are bonded to each other. For example, it means that in the case of nucleic acids, complementary nucleic acids are hybridized to each other, and in the case of proteins, two proteins are bonded to each other such as antigen-antibody reactions and interactions between proteins.

The term "detection substance" is a substance that functions as a sensor to detect a target substance, which exists as it is fixed to a detection surface. For example, it includes probe nucleic acids in the case of hybridization detection, and a predetermined protein in detection of interaction between proteins.

The term "target substance" is a substance to be a target for detection, which is a substance that interacts with the detection substance. Generally, it exists in a sample solution prepared from a biosample, and is dripped and supplied to a reaction system in bioassay.

The term "spot area" is a portion that is placed in wells arranged on the substrate surface. Generally, the detection substance is fixed to this portion, and the interaction between the detection substance and the target substance is developed in each portion.

According to an embodiment, means for increasing the detected amount of interaction can be provided in the case in which a bioassay substrate is used to detect the interaction between the detection substance and the target substance, and the detection accuracy and the signal-to-noise ratio can be improved.

Additional features and advantages are described herein, and will be apparent from, the following Detailed Description and the figures.

DETAILED DESCRIPTION

A bioassay substrate according to various embodiment is described below in greater detail with reference to the figures.

First, an exemplary bioassay substrate according to an embodiment will be described below with reference to FIGS. 1 to 3. In addition, each drawing shows examples, and the bioassay substrate according to an embodiment will not be restricted to those shown in the drawing in a limited way.

Figure 1:
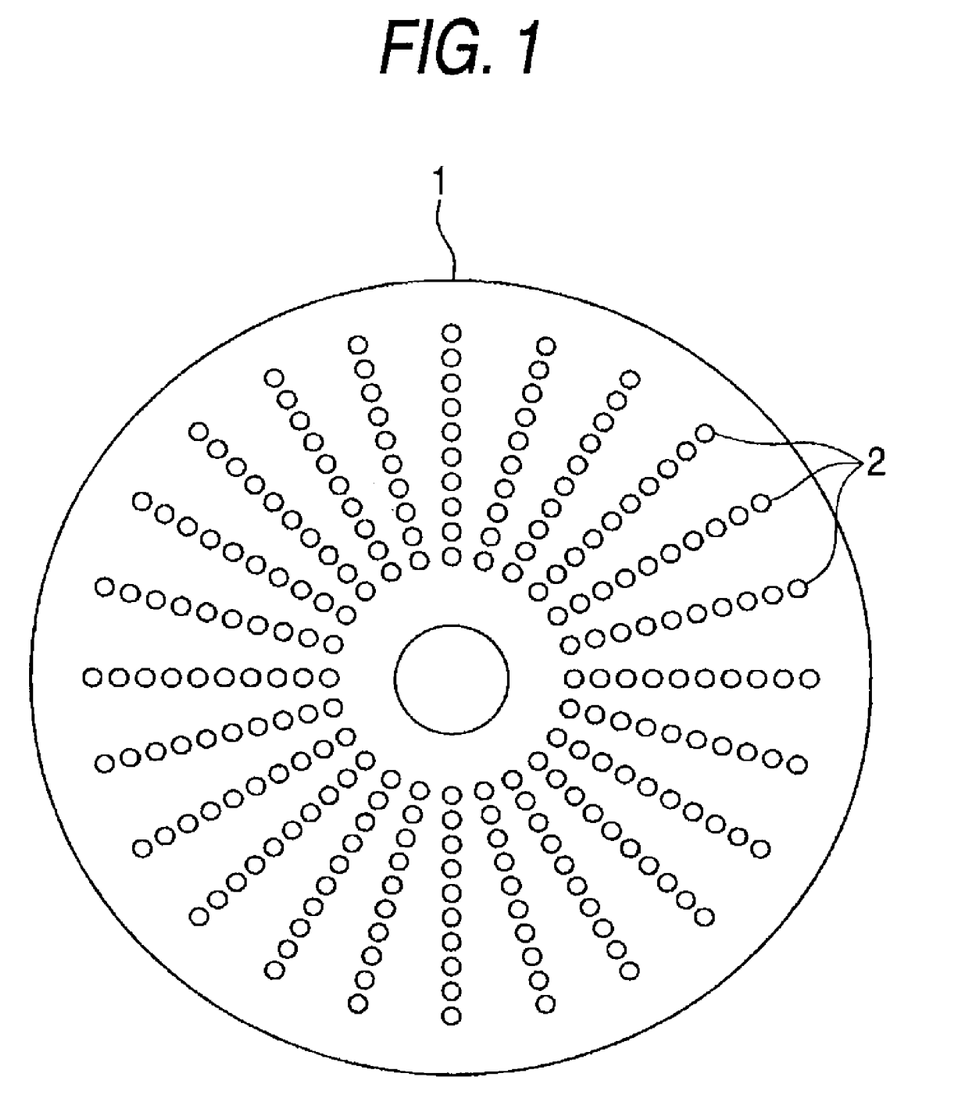
FIG. 1 shows a schematic diagram depicting the surface of a bioassay substrate.

FIG. 1 shows a schematic diagram depicting the surface of a bioassay substrate.

In FIG. 1, a plurality of wells 2 is formed on a disk-shaped substrate 1. In addition, the bioassay substrate according to an embodiment is not restricted only to a disk shape in a limited way. In addition, the number, position, depth and shape of the well 2 can be configured freely, which are not restricted in a limited way.

The materials of the substrate 1 are not restricted particularly, but a material that can transmit the excited ray having a predetermined wavelength (for example, fluorescent excitation rays) is preferable from a viewpoint in which excitation rays can be applied from the substrate side (the back side) in detecting interactions. For example, the similar base materials as those of known information recording media such as CD (compact disc), DVD (digital versatile disc), and MD (mini disc) can be used. These materials are preferable including glass such as quartz, polycarbonate, and polystyrene.

Figure 2:
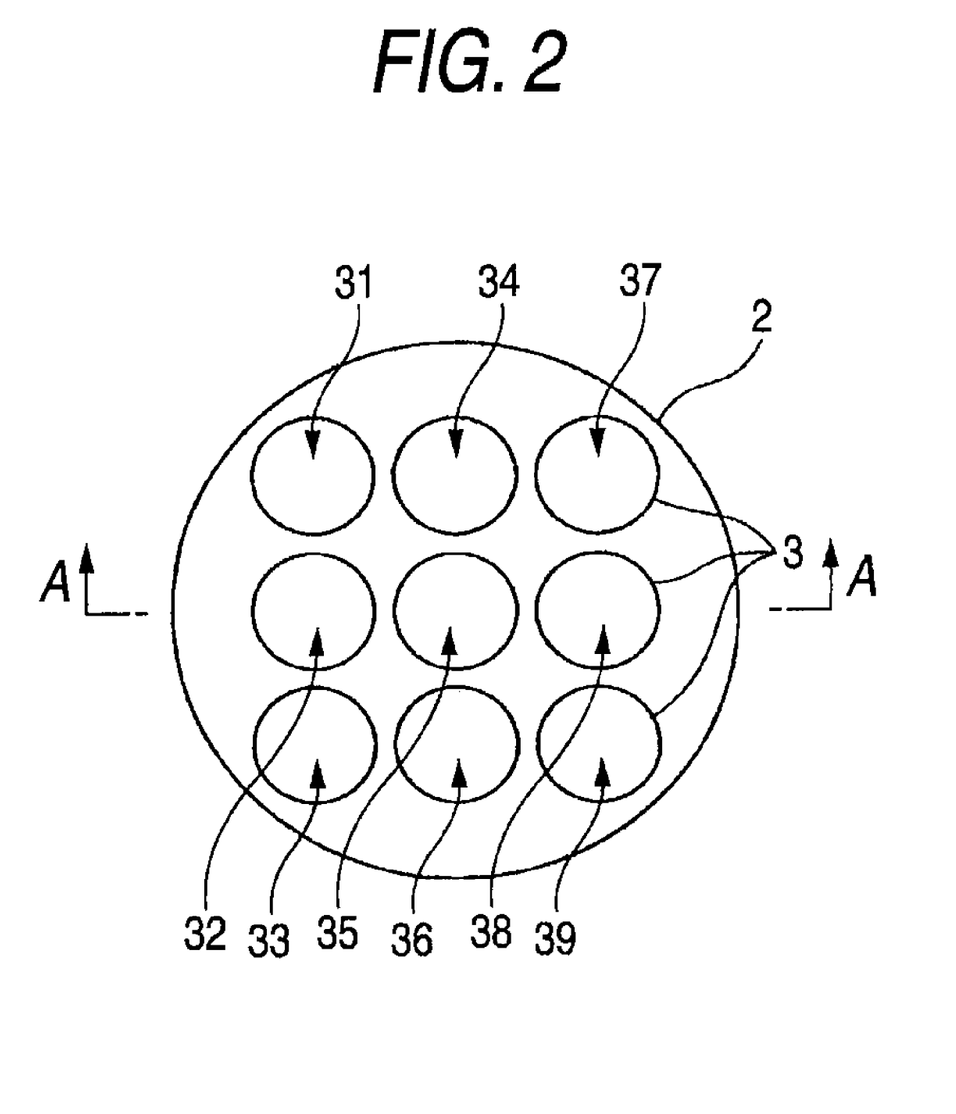
FIG. 2 shows a schematic diagram depicting one of wells formed on the surface of the bioassay substrate.

FIG. 2 shows a schematic diagram depicting one of the wells formed on the surface of the bioassay substrate.

A plurality of spot areas 3 is formed in the well 2. Then, the same type and the same amount of a detection substance is fixed in each of the spot areas 3.

For the detection substance, it is probe nucleic acids in the case of a DNA chip, and a predetermined protein such as an antibody in the case of a protein chip.

For example, in the case of fixing a probe nucleic acid, such a substance is used that has complementary base sequences to all or a part of the base sequence of a nucleic acid desired to detect. The probe nucleic acid depends on whether it is a synthetic nucleic acid, which is not restricted in a limited way. The chain length (mer number) can be set freely depending on purposes.

For example, in the case of fixing a protein, such a protein can be used that interacts with a protein desired to detect (including antibodies, enzymes, and receptors), or a polypeptide that contains at least a portion for interaction.

Means for fixing the detection substance is not particularly restricted and known method can be used. For example, this scheme may be performed in which the substrate surface is treated with avidin, the detection substance is biotinylated, and the detection substance is fixed in each of the spot areas on the substrate surface by avidin-biotin bonding. In addition, depending on the purposes, the detection substance may be fixed in each of the spot areas through a linker of a predetermined length.

In FIG. 2, nine spot areas (numerals 31 to 39) are placed in the well 2 in the unit of a predetermined number. For example, in bioassay using this substrate, the fluorescent excitation rays are applied in the unit of the spot areas to obtain fluorescent intensity in each of the spot areas. Then, the mean value of the fluorescent intensity is treated as the fluorescent intensity of the entire well. Thus, since variations in detection can be suppressed, the detection accuracy can be improved.

Figure 3:
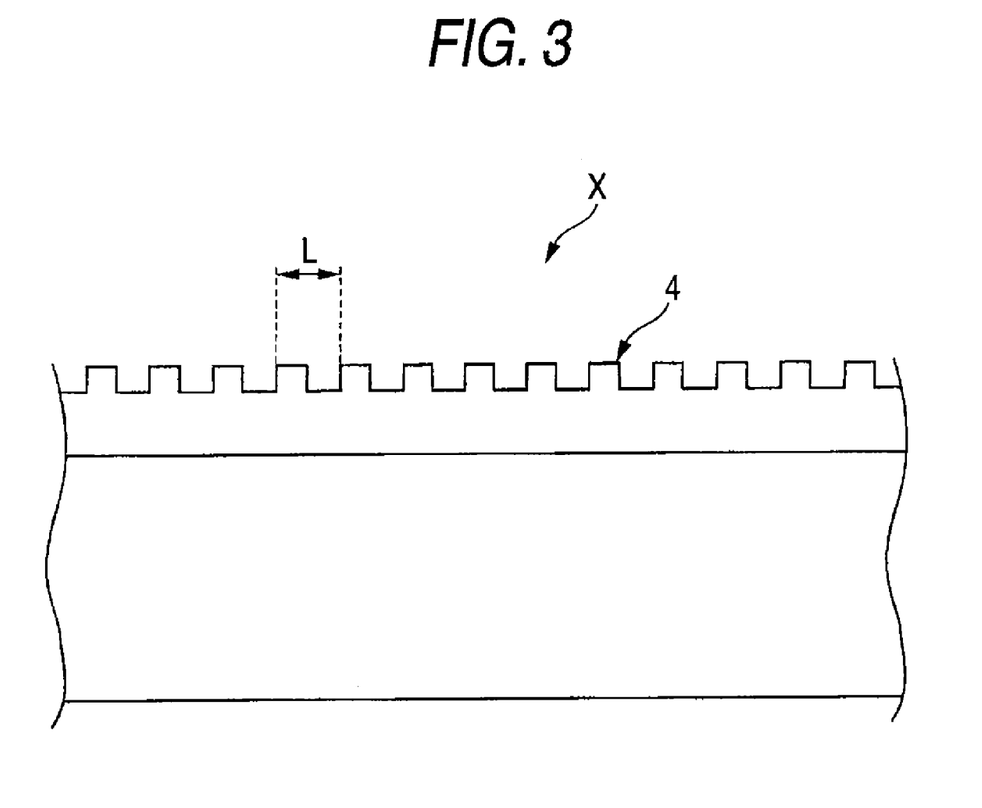
FIG. 3 shows a schematic diagram depicting a cross section of a spot area formed in the well.

FIG. 3 shows a schematic diagram depicting the cross section of the spot areas formed in the well.

In the bioassay substrate, a fine uneven structure 4 is continuously formed on a bottom surface 3a forming the spot areas 3. Thus, since the surface area for fixing can be increased, the amount of fixing the detection substance can be increased. Therefore, in the case in which a bioassay substrate is used to detect the interaction between the detection substance and the target substance, the detected amount of interaction (such as fluorescent intensity) can be increased, and the detection accuracy and the signal-to-noise ratio can be also improved.

For example, patterns of forming the uneven structure may be stripes in a lattice, a checker lattice, dots and so on. For example, these configurations can be formed in nano order using micromachining technique such as lithography, etching, nanoimprint, and injection molding.

The uneven structure may be formed so as to satisfy the Equation 1, where the track pitch length of the uneven structure is L, the wavelength of the fluorescent excitation ray emitted toward the bottom surface of the spot area is $\lambda(i)$, and the refractive index of the uneven structure is $n(i)$. Thus, since the diffracted light or the reflected light can be prevented from entering from the other spot areas, the detection accuracy and the signal-to-noise ratio can be improved in the case in which a bioassay substrate is used to detect the interaction between the detection substance and the target substance.

For example, in bioassay, there may be the case in which such a chip substrate is used that the refractive index at the wavelength 532 nm is 1.6 to bond a fluorochrome (such as Cy3) to DNA (the target substance), a fluorescent excitation ray of 532 nm is used to detect a fluorescence of about 550 to 650 nm to quantify hybridization. In this case, for example, the track pitch length of the uneven structure L is $\lambda/n$ or below (532/1.6=332 nm or below) and λ/10 or greater (532/10=53 or greater), whereby the advantages described above can be obtained.

A fabrication method of the bioassay substrate according to an embodiment

Next, an exemplary fabrication method of the bioassay substrate according to an embodiment will be described below.

For example, the bioassay substrate according to an embodiment can be fabricated in which wells are formed by the known technique described above the substrate, a plurality of spot areas is placed in the well by the unit of a predetermined number of spot areas, and a fine uneven structure is formed on the bottom surface of the spot areas.

As described above, for example, the uneven structure can be formed by using known micromachining techniques such as lithography, etching, nanoimprint, and injection molding.

Figure 4:
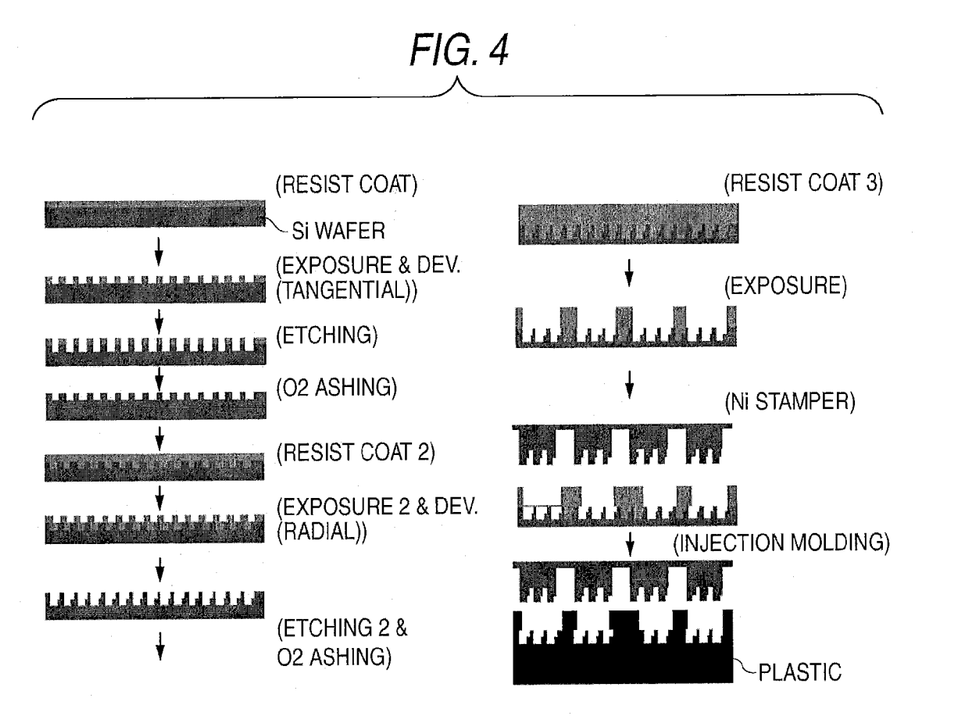
FIG. 4 shows a diagram depicting exemplary preparation process steps of a bioassay substrate.

FIG. 4 shows a diagram depicting exemplary preparation process steps of the bioassay substrate.

First, a photoresist and an electron resist are coated on a Si wafer (Si wafer), and a quartz glass plate (resist coat).

Subsequently, laser light and electron beam lithography are used to draw a desired micro lattice or dots for development ((tangential) exposure and development).

Then, a forming pattern of a predetermined structure is transferred to the substrate surface by dry etching or wet etching (etching), and the remaining resist is removed by $O_2$ plasma ashing ($O_2$ ashing).

Subsequently, a resist is again coated (resist coat 2) to draw a forming pattern such as lines orthogonal to the forming pattern or shifted by a half pitch therefrom for exposure and development ((radial) exposure 2 and development) and etching, and the pattern is transferred for ashing (etching 2 and $O_2$ ashing).

Then, in order to limit the area for fixing the detection substance, spot areas of a few microns to a few millimeters are formed by using a polyimide resist (resist coat 3 and exposure), and a master stamper is formed form the substrate by electroforming plating. In addition, for materials of the stamper, a known material such as nickel may be used.

Subsequently, the master stamper is used to perform nanoimprint transfer onto a glass or a resist, or to shape plastic (injection molding), whereby the bioassay substrate is formed in mass production at low costs.

Then, the same type and the same number of detection substances are fixed in each of the spot areas of the formed bioassay substrate by the know technique for use in bioassay.

A bioassay method according to an embodiment

Next, an exemplary bioassay method using the substrate according to an embodiment will be described below.

First, an objective sample solution is prepared from a biosample taken from a human body. In the case of the sample of a nucleic acid, for example, such a sample can be used that a nucleic acid is extracted, prepared and synthesized form a biosample by the known method. In this case, for example, a nucleic acid may be extracted from an objective sample for use, or a nucleic acid may be extracted from an objective sample to synthesize cDNA by the known method for use. Also in the case of the sample of a protein, for example, such a protein may be used that is extracted and prepared by the known method and dissolved in a buffer solution.

Subsequently, the sample solution is dripped and supplied onto each of the wells or each of the spot areas of the bioassay substrate. For example, the sample solution is dripped and supplied using a bioassay measuring device to determine precise positions as laser rays are used to focus and track them between the lens and the substrate.

Then, interactions between a detection substance and a target nucleic acid contained in the sample are developed in each of the wells or each of the spot areas, and then the interactions are detected by fluorescent intensity.

At this time, for example, the interaction may be detected by applying a fluorescent marker to the sample (target substance) in advance. In addition, in the case of hybridization detection, hybridization (double strand formation) of a nucleic acid for detection with a target nucleic acid may be detected by an intercalator.

The fluorescence is detected in which fluorescent excitation rays of a predetermined wavelength are applied onto each of the wells or each of the spot areas and the fluorescent intensity is detected at this time. For example, as means for emitting fluorescent excitation rays, a light source such as an LED is used.

Figure 5:
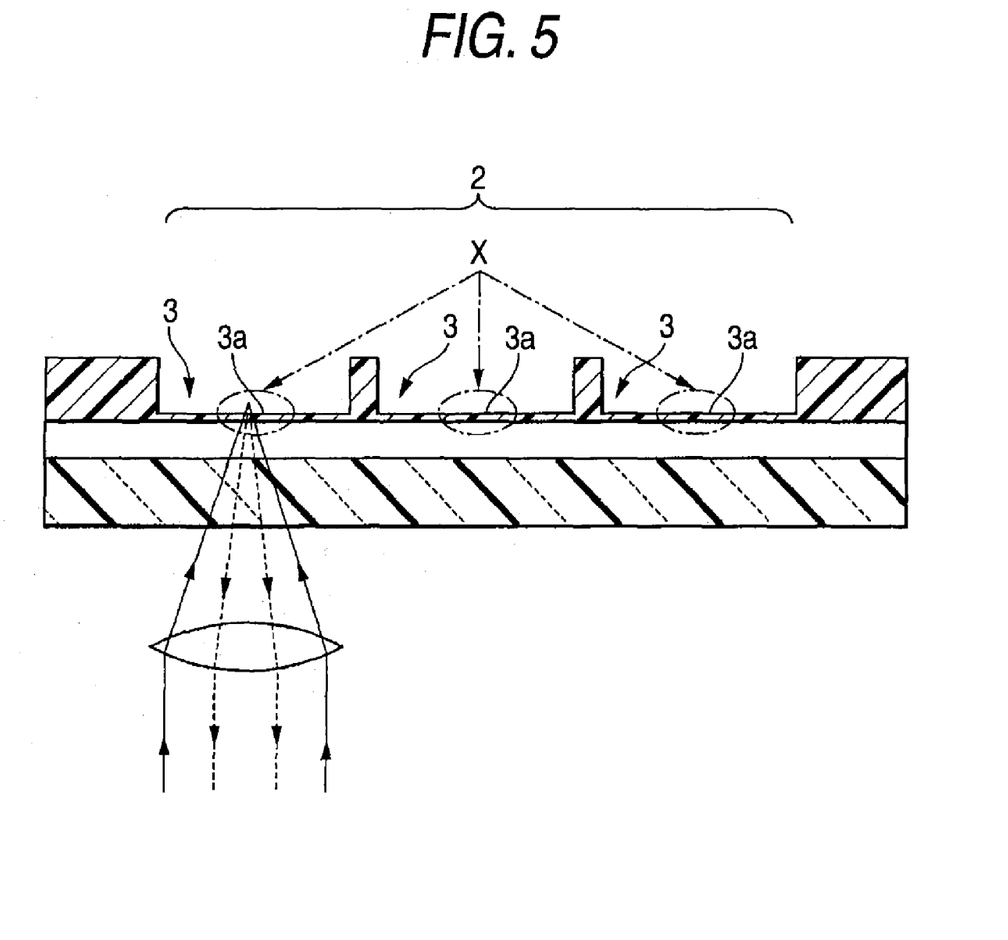
FIG. 5 shows a schematic diagram depicting the case in which fluorescent excitation rays are applied onto the bioassay substrate.

FIG. 5 shows a schematic diagram depicting when fluorescent excitation rays are applied onto the bioassay substrate. In addition, FIG. 5 schematically shows a cross section of A-A shown in FIG. 2.

As shown in FIG. 5, a plurality of the spot areas 3 is formed in the well 2 formed on the substrate surface. On the bottom surface 3a of the spot area 3, a detection substance (not shown) is fixed, and fluorescent excitation rays are applied onto the portion to detect the interaction between the detection substance and the target substance.

Fluorescent excitation rays X1 are applied onto the spot area 3 through an iris lens 5. When the detection substance and the target substance interact with each other, fluorescence substances emit fluorescence by the applied fluorescent excitation rays X1. The emitted fluorescence is again emitted through the iris lens 5 (sign X2). The fluorescence is detected by a fluorescence detecting unit, whereby the fluorescent intensity can be obtained.

In addition, in FIG. 5, the fluorescent excitation rays are applied from the back side of the substrate toward the spot area, and the fluorescence emitted from the spot area to the back side of the substrate is captured to detect the fluorescent intensity. In this case, since the light source and a fluorescent intensity measuring unit of the bioassay measuring device can be disposed on the back side of the substrate, an advantage is provided that the device configuration can be simplified.

In the case of detecting the fluorescent intensity, for example, this scheme may be performed in which fluorescent excitation rays are applied in the unit of the spot area, the fluorescent intensity is detected for every spot area, and the mean value of the fluorescent intensity in each of the spot areas is the fluorescent intensity of the well. Thus, since variations in detection can be suppressed, the detection accuracy can be improved.

In the case of detecting the fluorescent intensity, the incident angle of the fluorescent excitation rays X1 can be set freely. In the case of the bioassay substrate according to an embodiment, the bottom surface 3a of the spot area 3 is provided with the fine uneven structure. Then, based on the S-polarization and the P-polarization, the oscillating direction of the fluorescent excitation rays X1 is selected to control polarization, whereby the light intensity of the fluorescent excitation rays can be controlled.

EXAMPLE 1

Example 1 shows an exemplary bioassay substrate according to an embodiment.

A disk-shaped bioassay substrate was prototyped in accordance with the fabrication method of the bioassay substrate.

Figure 6A:
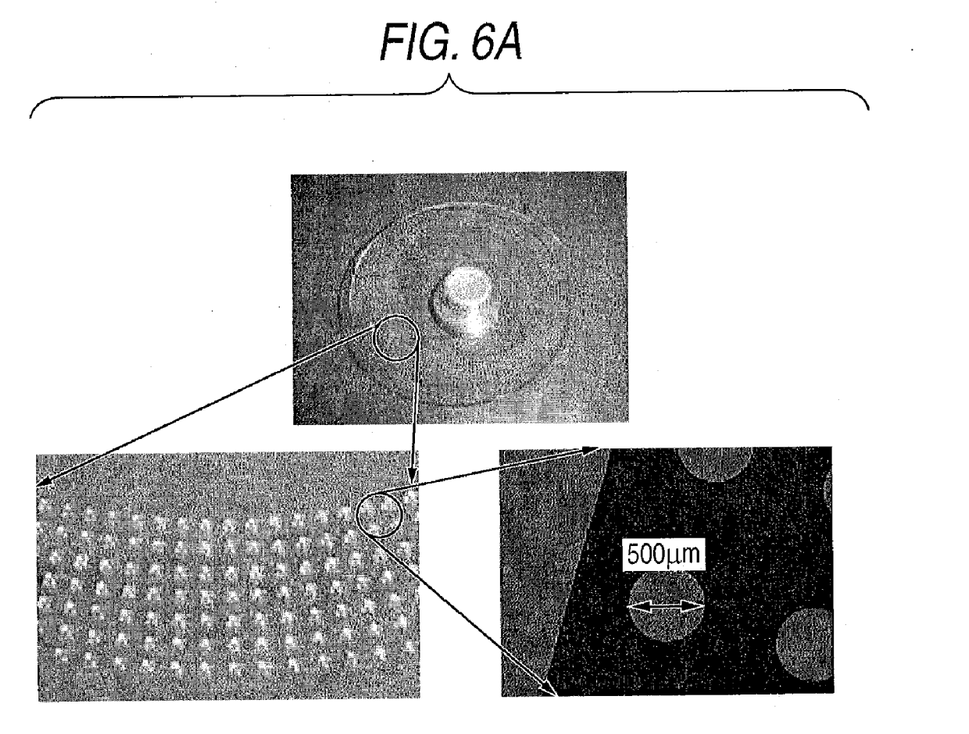
FIG. 6A illustrates a substitute for diagrams depicting a prototype bioassay substrate and enlarged parts thereof.

FIG. 6A illustrates a substitute for a diagram depicting a prototype bioassay substrate and a partially enlarged part thereof. In FIG. 6A, 180 reaction areas are regularly arranged in a disk-shaped glass substrate. The diameter of each of the reaction area is 500 μm, and the height is 5 μm.

Figure 6B:
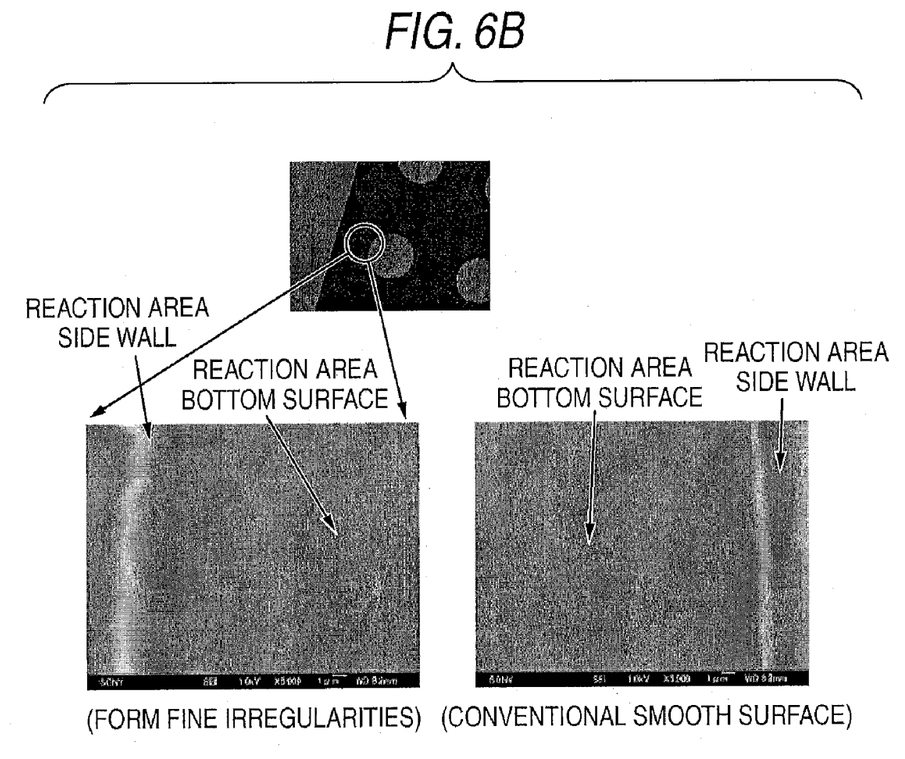
FIG. 6B illustrates a substitute for diagrams depicting a further enlarged one of reaction areas shown in FIG. 6A.

FIG. 6B illustrates a substitute for a diagram depicting an enlarged one of the reaction areas shown in FIG. 6A. In the left photograph in FIG. 6B, the fine uneven structure is formed on the bottom surface of the reaction area. In addition, the right photograph shows a related art smooth surface on which no fine uneven structure is formed.

Figure 6C:
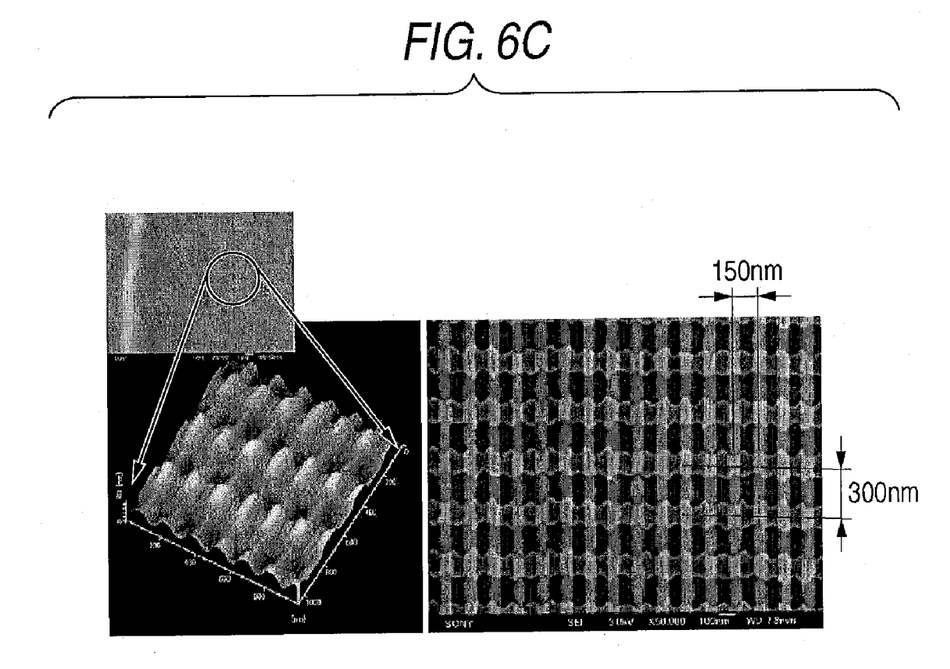
FIG. 6C illustrate three dimensional irregularities that the uneven structure shown in FIG. 6B is measured by AFM and its electron photomicrograph.

FIG. 6C illustrates three dimensional irregularities that the uneven structure shown in FIG. 6B is measured by AFM and its electron photomicrograph. In FIG. 6C, grooves of a track pitch of 150 nm are formed in the radial direction, and grooves of a pitch of 300 nm are formed in the circumference direction.

Figure 6D:
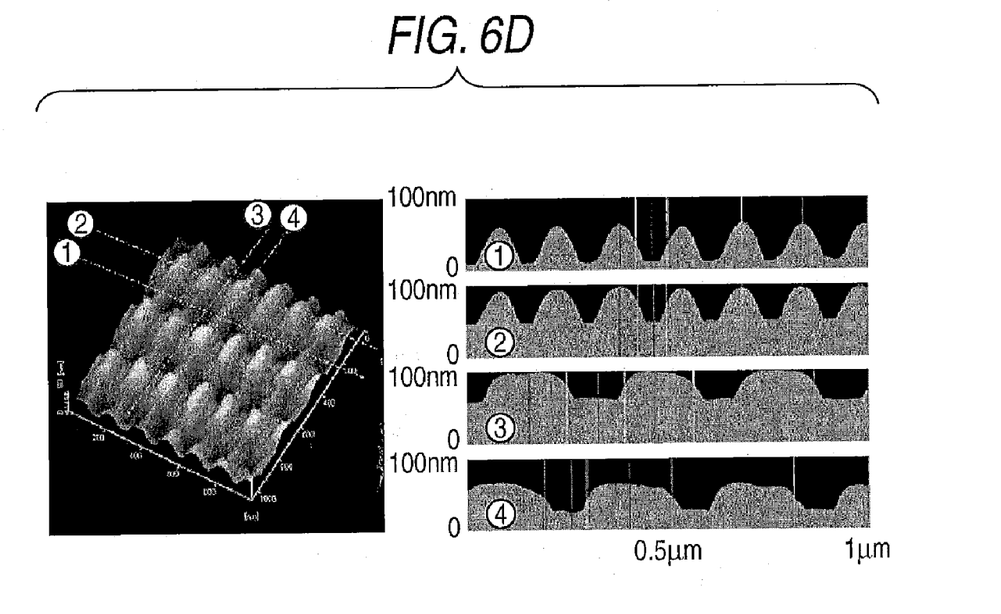
FIG. 6D shows cross sectional AFM images of the AFM uneven structure shown in FIG. 6C.

FIG. 6D shows cross sectional AFM images of the AFM uneven structure shown in FIG. 6C.

As the result of analysis based on FIG. 6D, it was revealed that the uneven structure is formed in this manner, whereby the surface area of the reaction area is about twice as much as the related art smooth surface. This result shows that the fine uneven structure in nano order is continuously formed in the reaction area to increase the surface area for fixing, that is, the amount of fixing the detection substance in the spot area can be increased.

According to an embodiment, in the case in which a bioassay substrate is used to detect the interaction between the detection substance and the target substance, means for increasing the detected amount of interaction can be provided, and the detection accuracy and the signal-to-noise ratio can be improved. Therefore, an embodiment is useful for the technique using bioassay substrates such as a DNA chip, and a protein chip.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A bioassay substrate in which a sample solution is dripped onto a spot area to which a plurality of detection substances is fixed and an interaction between the detection substance and a target substance in the sample solution is detected by fluorescent intensity, the substrate comprising:

a predetermined number of the spot areas placed in a well formed on a top surface of the substrate, each seperate spot area having a plurality of detection substances fixed to a bottom surface, the bottom surface having a fine uneven structure continuously formed therein so as to provide an increased surface area of each of the spot areas configured to fix the plurality of detection substances.

2. The bioassay substrate according to claim 1, wherein an equation expressed in Equation 1 is satisfied, where a track pitch length of the uneven structure is L, a wavelength of a fluorescent excitation ray emitted toward the bottom surface of the spot area is λ(i), and a refractive index of the uneven structure is n(i):

$$L < \lambda(i)/n(i).$$  Equation 1

3. The bioassay substrate according to claim 1, wherein the fine uneven structure is formed in the bottom surface by a technique selected from the group consisting of: lithography, etching, nanoimprint and injection molding.

\* \* \* \* \*